United States Patent
Huie, Jr. et al.

(10) Patent No.: US 7,255,871 B2
(45) Date of Patent: Aug. 14, 2007

(54) NANOTUBE MAT WITH AN ARRAY OF CONDUITS FOR BIOLOGICAL CELLS

(75) Inventors: Philip Huie, Jr., Cupertino, CA (US); Harvey A. Fishman, Menlo Park, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 475 days.

(21) Appl. No.: 10/431,334

(22) Filed: May 6, 2003

(65) Prior Publication Data

US 2004/0048365 A1     Mar. 11, 2004

Related U.S. Application Data

(60) Provisional application No. 60/379,139, filed on May 8, 2002, provisional application No. 60/379,067, filed on May 8, 2002.

(51) Int. Cl.
| | |
|---|---|
| *A61F 2/00* | (2006.01) |
| *C12N 5/00* | (2006.01) |
| *C12M 1/00* | (2006.01) |
| *C12Q 1/00* | (2006.01) |

(52) U.S. Cl. .......................... 424/423; 435/4; 435/325; 435/395; 435/283.1

(58) Field of Classification Search .................... None
See application file for complete search history.

(56) References Cited

U.S. PATENT DOCUMENTS 6,670,179 B1 *  12/2003  Mattson et al. ............. 435/325

OTHER PUBLICATIONS

Mark C Peterman et al., "Building thick photoresist structures from the bottom up," J. Micromeck. Microeng. 13 (2003) 380-382.

* cited by examiner

*Primary Examiner*—David M. Naff
(74) *Attorney, Agent, or Firm*—Lumen Intellectual Property Services, Inc.

(57) ABSTRACT

A nanotube mat is provided with an array of conduits to support, direct growth, select or interface one or more biological cells or cell processes. The carbon nanotube mat provides mechanical stability, is biocompatible, will support cell growth, can desirably be derivatized with growth factors, molecules, nutrients, inhibitory factors, ligands, transduction molecules or morphogenic factors, and would allow the formation of conduits to guide cells and cell extensions to be hosted or grown. The conduits could take any size or shape to support, direct growth, select or interface one or more cells or processes. In general the conduits could be channels, discontinuous channels, tapered channels or walls. The nanotube mat could be used to interface biological cells with other cells, tissue or structures that have electrical, mechanical, magnetic means, or optical means. The nanotube mat could also incorporate chemicals, analytes, drugs, lips, carbohydrates, secretory products or the like.

33 Claims, 16 Drawing Sheets

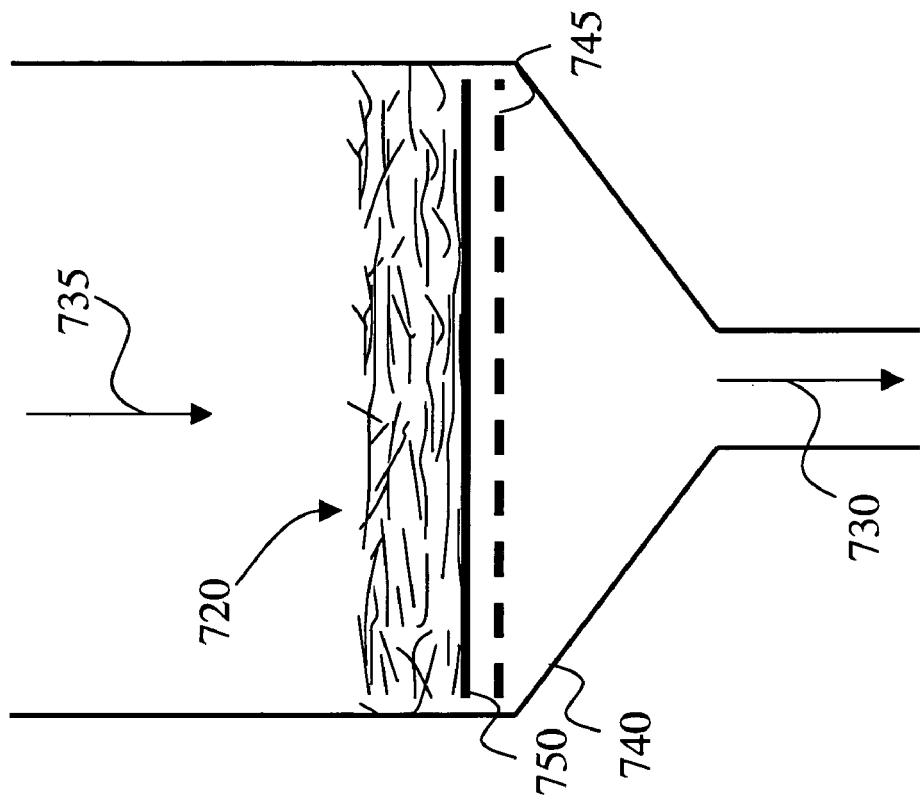

NANOTUBE MAT WITH AN ARRAY OF CONDUITS FOR BIOLOGICAL CELLS

CROSS-REFERENCE TO RELATED APPLICATIONS

This application is cross-referenced to and claims priority from U.S. Provisional application No. 60/379,139 filed May 8, 2002 and U.S. Provisional application No. 60/379,067 filed May 8, 2002 which are hereby incorporated by reference.

FIELD OF THE INVENTION

The present invention relates generally to cell and tissue engineering. More particularly, the present invention relates to nanotube mats for supporting, organizing, growing or interfacing biological cells, cell processes or agents.

BACKGROUND

Cell and tissue engineering is an emerging field with solutions being directed to control, growth, hosting or interfacing of cells. There is however a need to develop devices to support cells in the third dimension. For instance, in a neural prosthesis it would be desired to incorporate a stable and biocompatible interface with conduits to allow neural cells to grow on or through the conduits. The neural cells that grow on or through the conduits of the neural prosthesis could then functionally be in contact with other cells, tissue or devices, and potentially restore functionality of the lost or deteriorated cells.

One solution for developing such a device is the use of hydrogel membranes. However, hydrogel membranes may not be suitable for use as a lamina to support the arraying of cells and also cell growth in the third dimension. Hydrogels such as Matrigel (a collagen sol/gel) will dissolve over a period of days and are mechanically fragile. They are also difficult to handle in the form of, for instance, a 100-micron thick membrane. Furthermore, they become unstable when conduits are introduced into the membrane. Another drawback of using hydrogel membranes is that they are a proteinacious. Furthermore, these membranes tend to stick to molds and therefore releasing compounds must be used to separate the hydrogel casting from, for instance, a SU-8 mold which might distort the final casting of the membrane with conduits. The hydrogel matrix material may also be immunogenic and could stimulate a host's immune system leading to inflammation and ultimate failure of the device. Accordingly, the art is in need for new devices and methods that are mechanically more stable, biocompatible, and are easier to develop.

SUMMARY OF THE INVENTION

The present invention provides a nanotube mat with an array of conduits. The nanotube mat could support or host biological cells or cell processes. The nanotube mat could also direct growth of biological cells or cell processes. The nanotube mat could further be used to organize, select or interface biological cells or cell processes with structures or devices that have electrical, mechanical, magnetic, or optical means. In general, the nanotube mat allows for support or selection of biological cells or cell processes as well as of agents such as chemicals, analytes, drugs, secretory products or the like.

Carbon nanotubes that are used to develop the nanotube mats provide mechanical stability, are biocompatible, will support cell growth, can desirably be derivatized with growth factors, molecules, nutrients, inhibitory factors, ligands, transduction molecules or morphogenic factors, and would allow the formation of conduits to guide cells and cell extensions to be hosted or grown. The conduits could take any shape or size to direct growth, support, select or interface one or more cells. In general the conduits could be channels, discontinuous channels, tapered channels, walls or the like. Furthermore, multiple nanotube mats could be layered to create a multi-laminate array system.

BRIEF DESCRIPTION OF THE FIGURES

The objectives and advantages of the present invention will be understood by reading the following detailed description in conjunction with the drawings, in which:

FIGS. 7A-B show exemplary methods of developing a nanotube mat according to the present invention;

DETAILED DESCRIPTION OF THE INVENTION

Although the following detailed description contains many specifics for the purposes of illustration, anyone of ordinary skill in the art will readily appreciate that many variations and alterations to the following exemplary details are within the scope of the invention.

Accordingly, the following preferred embodiment of the invention is set forth without any loss of generality to, and without imposing limitations upon, the claimed invention.

The present invention provides a nanotube mat with an array of conduits. In one aspect, the device is a nanotube mat to support or host biological cells or cell processes. In another aspect, the device is a nanotube mat to direct growth of biological cells or cell processes. In yet another aspect, the device is a nanotube mat capable of organizing or selecting biological cells or cell processes. In still another aspect, the device is a nanotube mat capable of interfacing biological cells or cell processes with structures or devices of electrical, mechanical, optical or combination of such electrical, mechanical, optical structures or devices. In general, the nanotube mat allows for one or more biological cells to be arranged. Examples of biological cells are, for instance, related to any type of tissue with neural connections, such as, but not limited to, muscle, sphincters, bladder, any excitable tissue, such as hormone secreting glands, or the like. Biological cells without neural connections could also be used in combination with the nanotube mat of the present invention, for instance, to engineer cells or tissue.

The conduits could be sized and shaped to accommodate the type of cell(s) or process(es) that one would like to growth, support, organize or interface with the nanotube mat. The shape of the conduits is typically guided by the functionality one would like to obtain from the nanotube mat. The diameter of a conduit could be as small as the size of at least one biological cell or at least one cell process. The height of a conduit could also be as small as the size of a biological cell, as short as a cell process, or sized to accommodate the combined size of a group of cells. The conduits could be all the way through the thickness of the nanotube mat or could be partially through the thickness of the nanotube mat therewith providing cups (e.g. the cup height could be, but not limited to, 2 microns to 50 microns). The nanotube mat could be small such as, for instance, in a millimeter range in application related to a fovea or large such as, for instance, in industrial applications.

Figure 1:
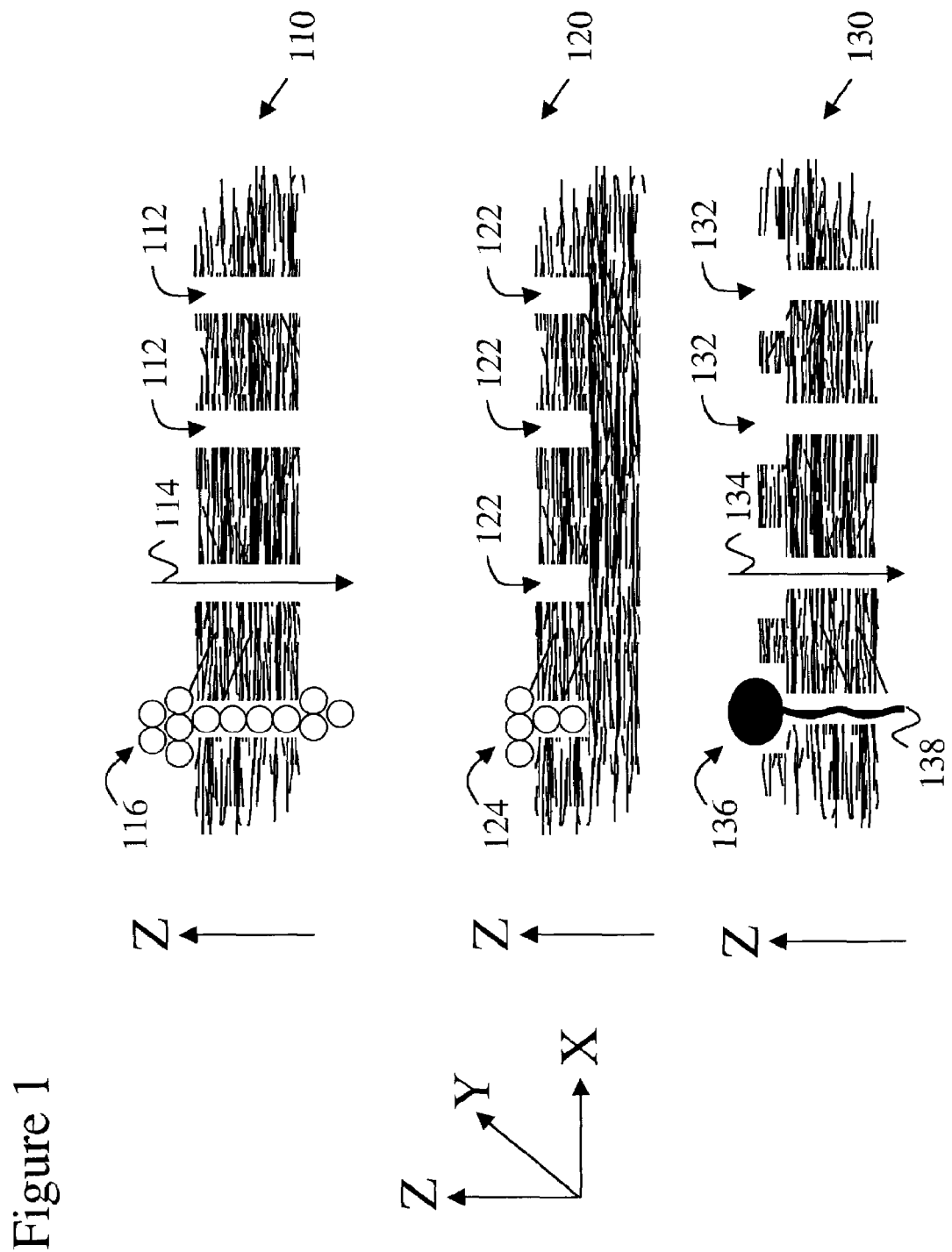
FIGS. 1-6 show examples of nanotube mats with conduits according to the present invention.
Figure 2:
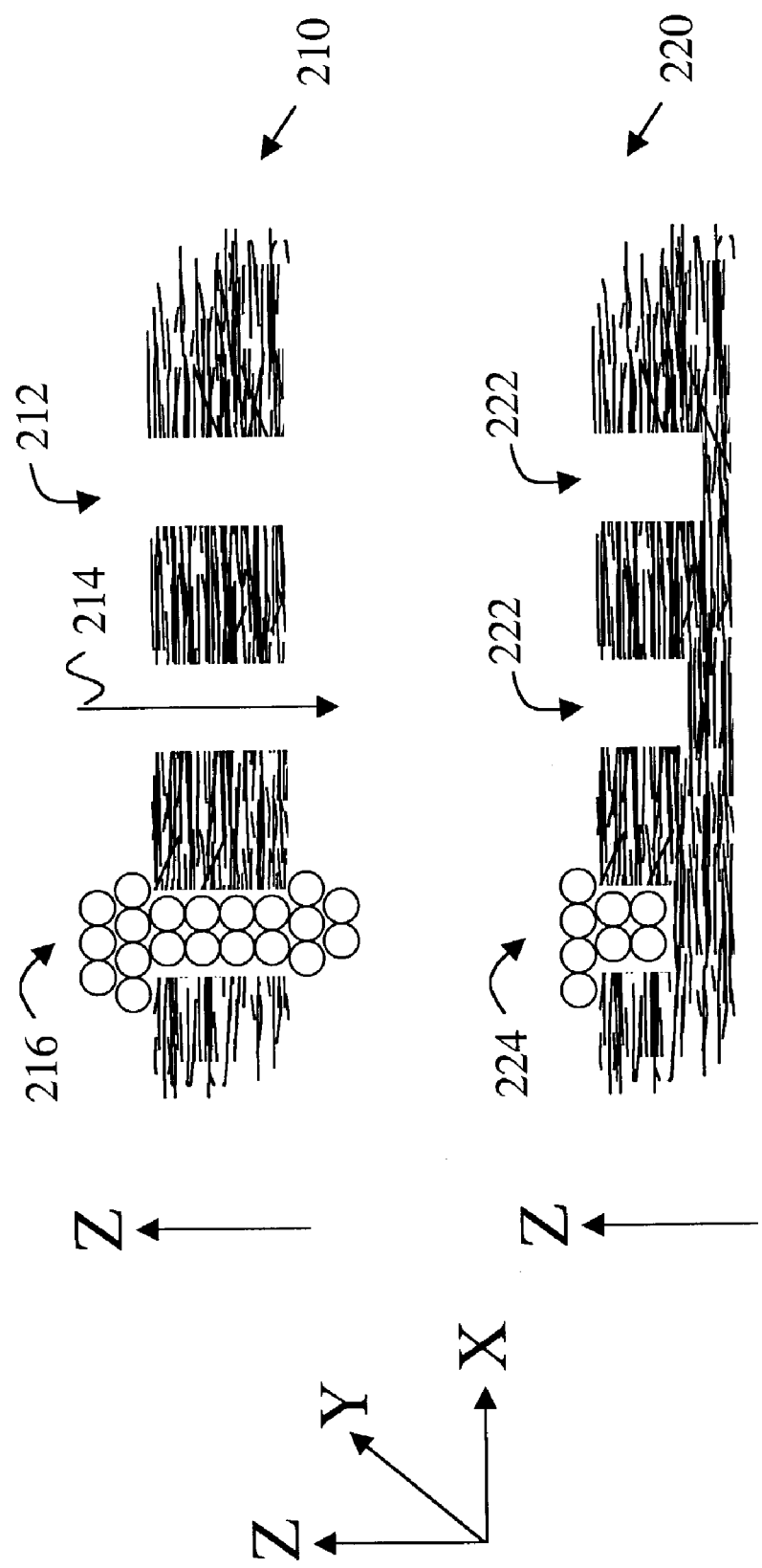

FIG. 1 shows examples of nanotube mats 110, 120, 130 with different types of conduits. The Z-direction shows the thickness of nanotube mats 110, 120, 130. Nanotube mat 110 shows conduits 112 useful to direct growth 114 of biological cells 116 through the thickness of nanotube mat 110. Nanotube mat 120 shows conduits 122 partially through the thickness of nanotube mat 120 to host or support biological cells 124 in conduits 122. Nanotube mat 130 shows conduits 132 to direct growth 134 of part of a biological cell 136 (e.g. a neural cell) through the thickness of nanotube mat 130. Note that conduits 132 have two different dimensions in which the smaller could be used to prevent a cell to go entirely through the conduit 132 and therewith provide selectivity of growth (e.g. to allow a neurite 138 to grow or extend further through the conduits 132). For the purposes of this invention, such a conduit is also referred to a discontinuous channel. Discontinuous channels could also be L-shaped, rectangular, square or any type of shape that is not continuous. FIG. 2 shows examples of nanotube mats 210, 220 similar to nanotube mats 110, 120 as shown in FIG. 1, respectively. The difference is that conduits 212, 222 of nanotube mats 210, 220 have a larger diameter compared to conduits 112, 122 nanotube mats 110, 120, respectively. Conduits 212 allow direct growth 214 of a larger group of biological cells 216 through the thickness of nanotube mat 210 compared to nanotube mat 110. Conduits 222 allow for support or hosting of a larger group of biological cells 224 compared to nanotube mat 120.

Figure 3:
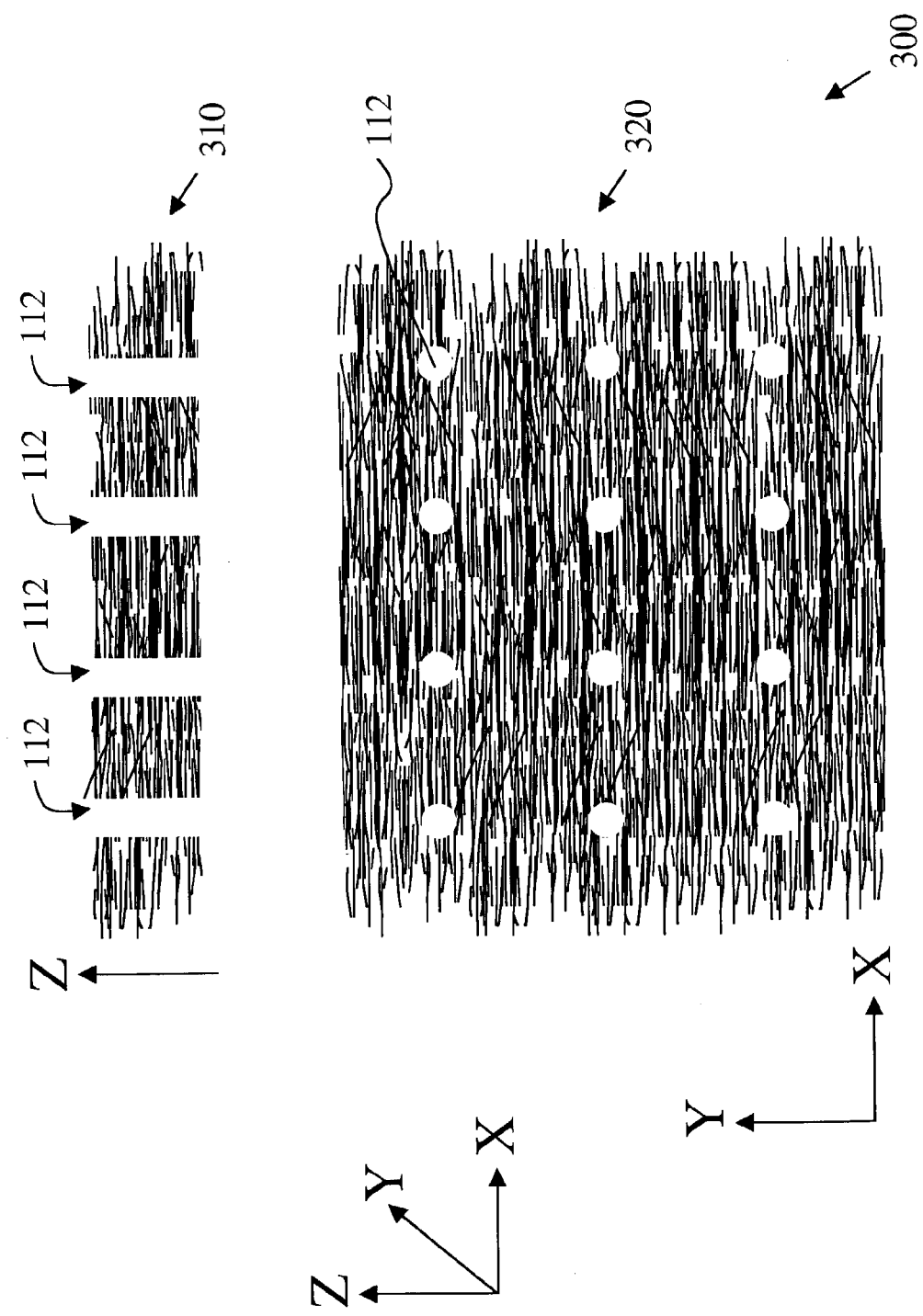
Figure 4:
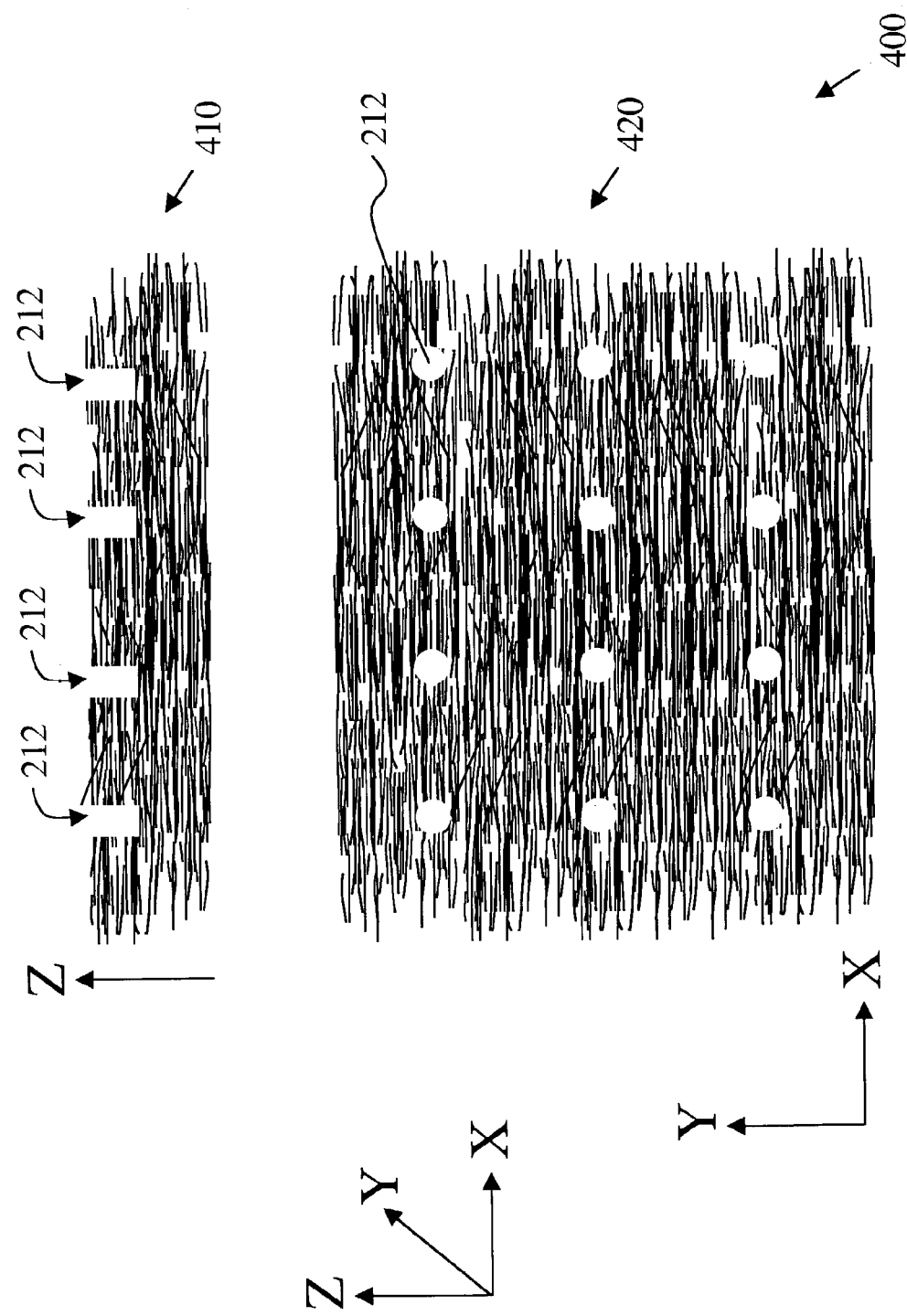
Figure 5:
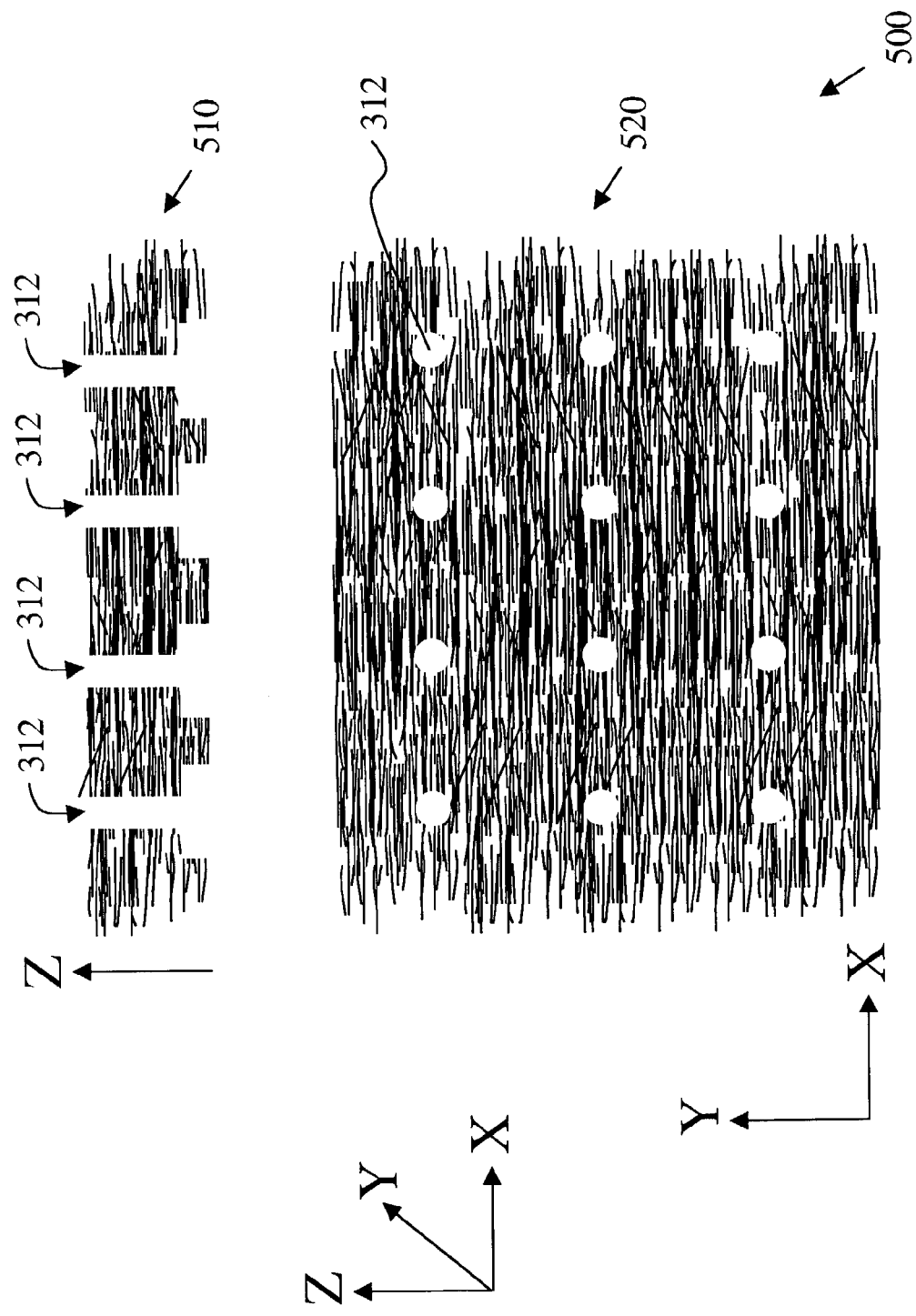
Figure 6:
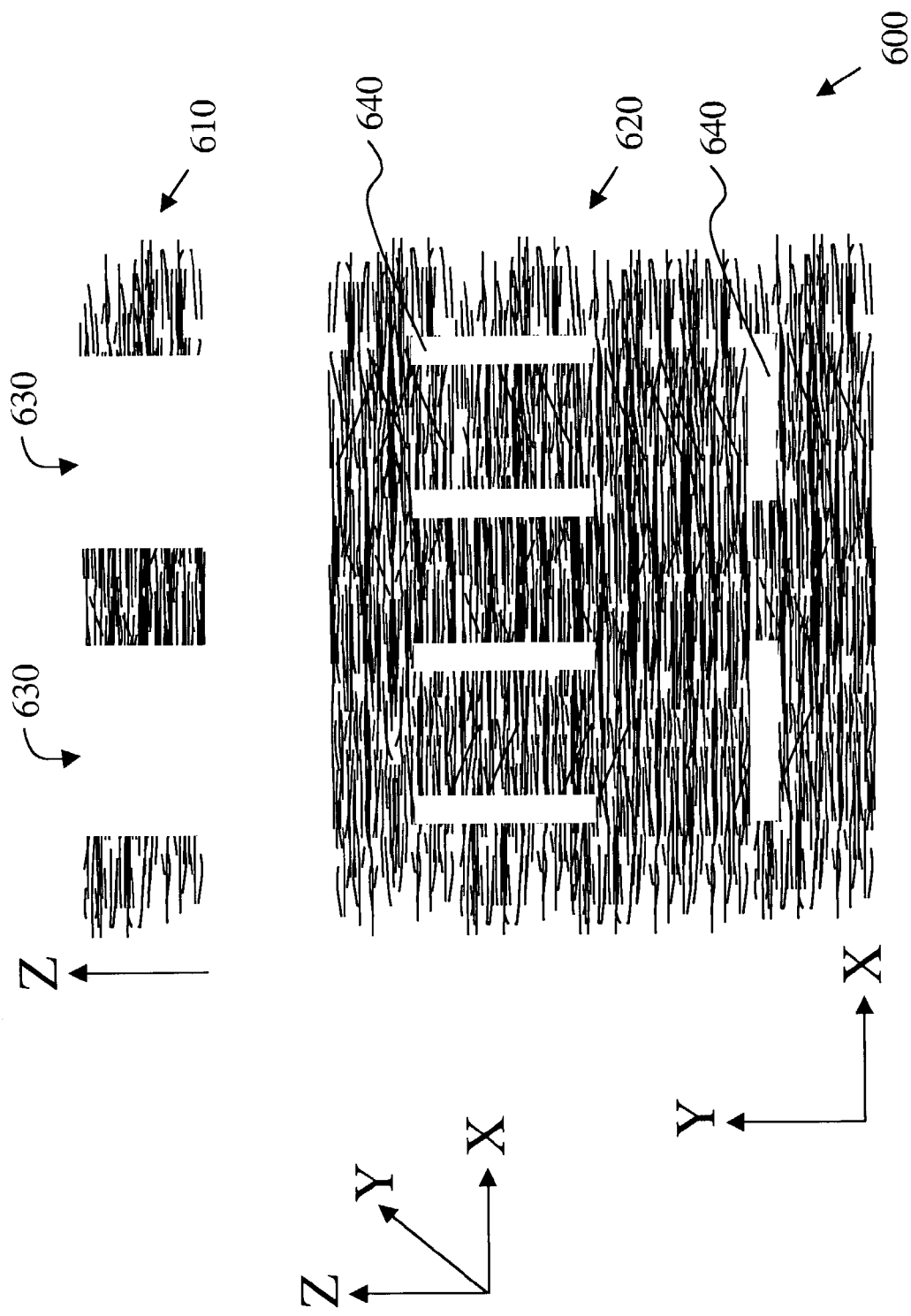

FIG. 3 shows a side view 310 (Z-direction) and a top view 320 (X-direction and Y-direction) of an array of conduits 112 of nanotube mat 110 as shown in FIG. 1. FIG. 4 shows a side view 410 (Z-direction) and a top view 420 of an array of conduits 212 of nanotube mat 120. FIG. 5 shows a side view 510 (Z-direction) and a top view 520 (X-direction and Y-direction) of an array of conduits 132 of nanotube mat 130. The conduits could be organized in any type of array and is not limited to an orderly spacing of conduits as shown in the examples of FIGS. 1-5. The number of conduits per nanotube mat could range from a few to many depending on the type of applications. Furthermore, the type of conduits that could be used is not limited to one particular kind of conduits since it would be possible to combine different sizes and shapes of conduits in one array of a nanotube mat. For instance, FIG. 6 shows an example of a side view 610 (Z-direction) and a top view 620 (X-direction and Y-direction) of an array of conduits 630, 640 of nanotube mat 600. Conduits 630, 640 are now walls that could be arranged differently as shown in FIG. 6 to support biological cells in different directions or direct growth in different directions. Other examples of shapes of possible conduits include, for instance, tapered or cone-shaped, L-shaped conduits, square conduits or rectangular conduits. Tapered or cone-shaped conduits could also be used to restrict particular cells to pass or grow through the conduit, and therewith could provide selectivity of cells.

The nanotube mats could be developed from carbon nanotubes or any other type of nanotubes, which are commercially available and preferably purified, such as, for example, but not limited to, single wall nanotubes, multi-wall nanotubes, bamboo nanotubes, or the like. The types of carbon nanotubes that could be considered as material for the nanotube mat of the present invention are the ones that provide mechanical stability, are biocompatible, will support cell growth, can potentially be derivatized with growth factors, molecules, nutrients, inhibitory factors, ligands, transduction molecules or morphogenic factors, and would allow the formation of conduits to guide cells and cell extensions/processes to be hosted or grown. The difference between single-wall carbon nanotubes or multi-wall carbon nanotubes would provide a difference in compliance of the resulting nanotube mat, whereby the use of multi-wall carbon nanotubes would results in a less compliant nanotube mat.

A slurry of purified, dispersed carbon nanotubes 720 could be filtrated, vacuumed or by means of using positive pressure to push 735 or pull 730 the slurry of carbon nanotubes 720 to create a nanotube mat (See FIG. 7A). The means of filtration, vacuuming or positive pressure means are known in the art, and there is no preference for each of these methods as long as the method is capable to push 735 or pull down 730 the slurry of carbon nanotubes. A funnel 740, for instance a Buchner funnel with a filter support 745, an inline filter, or any other filter or filter holder known in the art, could be used. A filter 750 could be positioned inside funnel 740 or filter holder, such as a polycarbonate filter or any other filter known in the art as long as the filter disallows the carbon nanotubes to pass through and allows the liquid from the slurry to pass through.

Figure 8A:
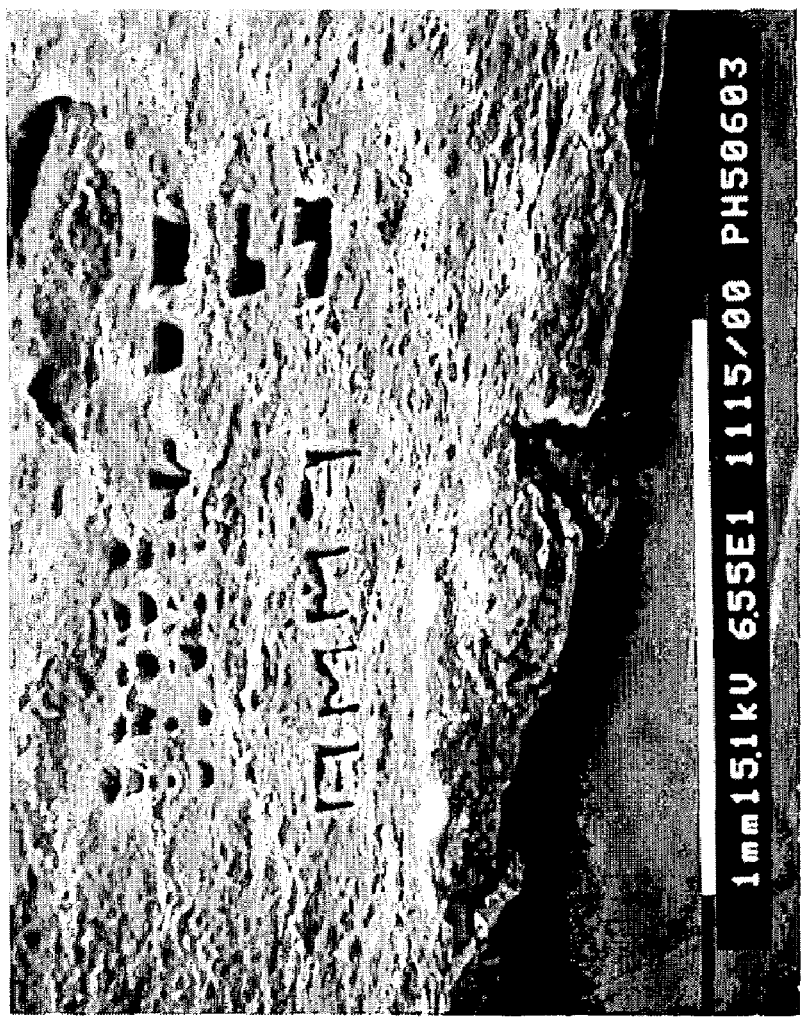
FIGS. 8A-C show examples of nanotube mats with conduits developed with laser ablation according to the present invention.
Figure 8B:
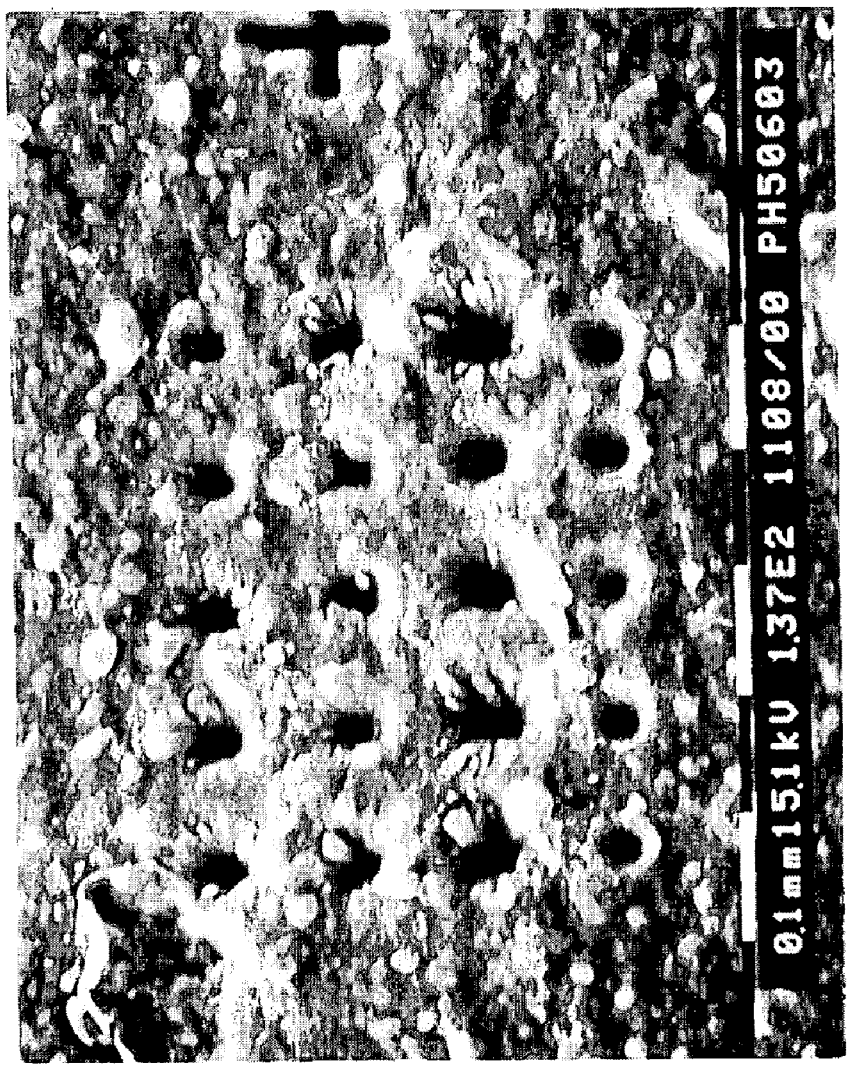
Figure 8C:
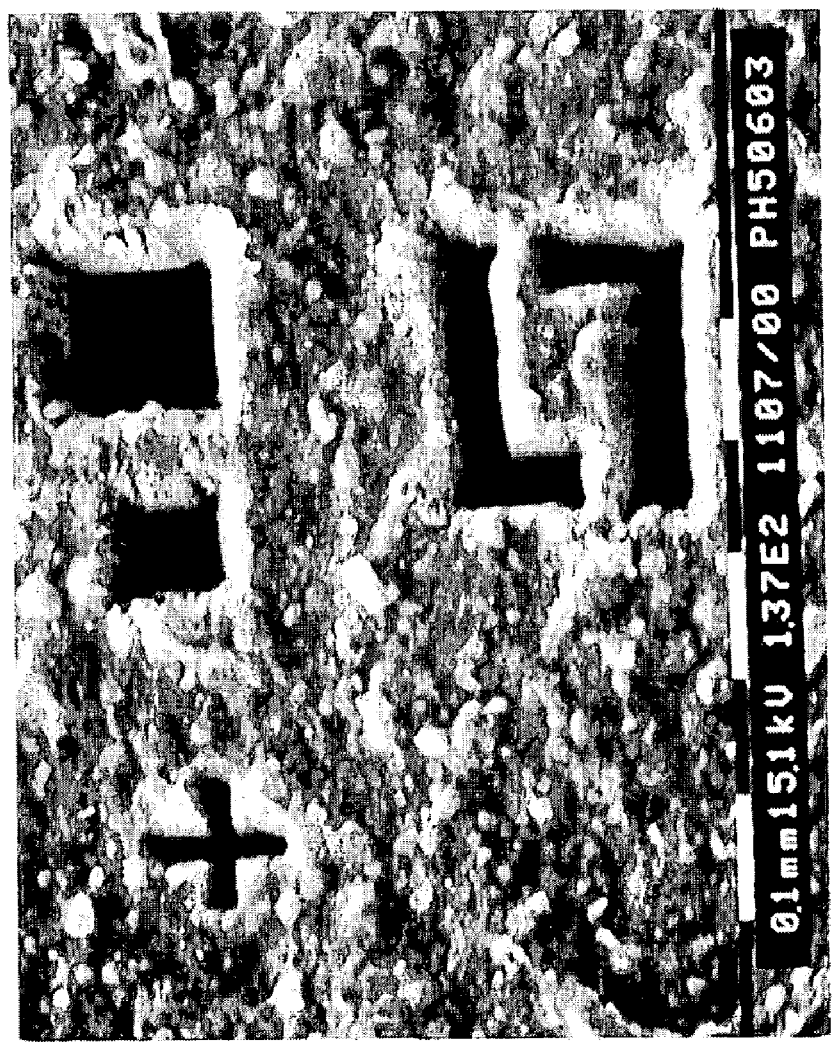

In one aspect, conduits in a nanotube mat could be created by laser ablation. Laser ablation would allow one to control the development of a desired shape (channels, discontinuous channels, squares, rectangular, L-shape, cone-shape, etc.), size, array and depth (for instance for cups or multi-layered conduits) of a conduit. Any type of laser could be used that is capable of ablating through or partly through the carbon nanotube mat such as, but not limited to, a Ti-sapphire laser. A short pulse could be used typically at a lower power sufficient enough to create the desired conduits. FIG. 8 shows examples of nanotube mats with different shapes and sizes of conduits developed with laser ablation using a Ti-sapphire laser.

Figure 7B:
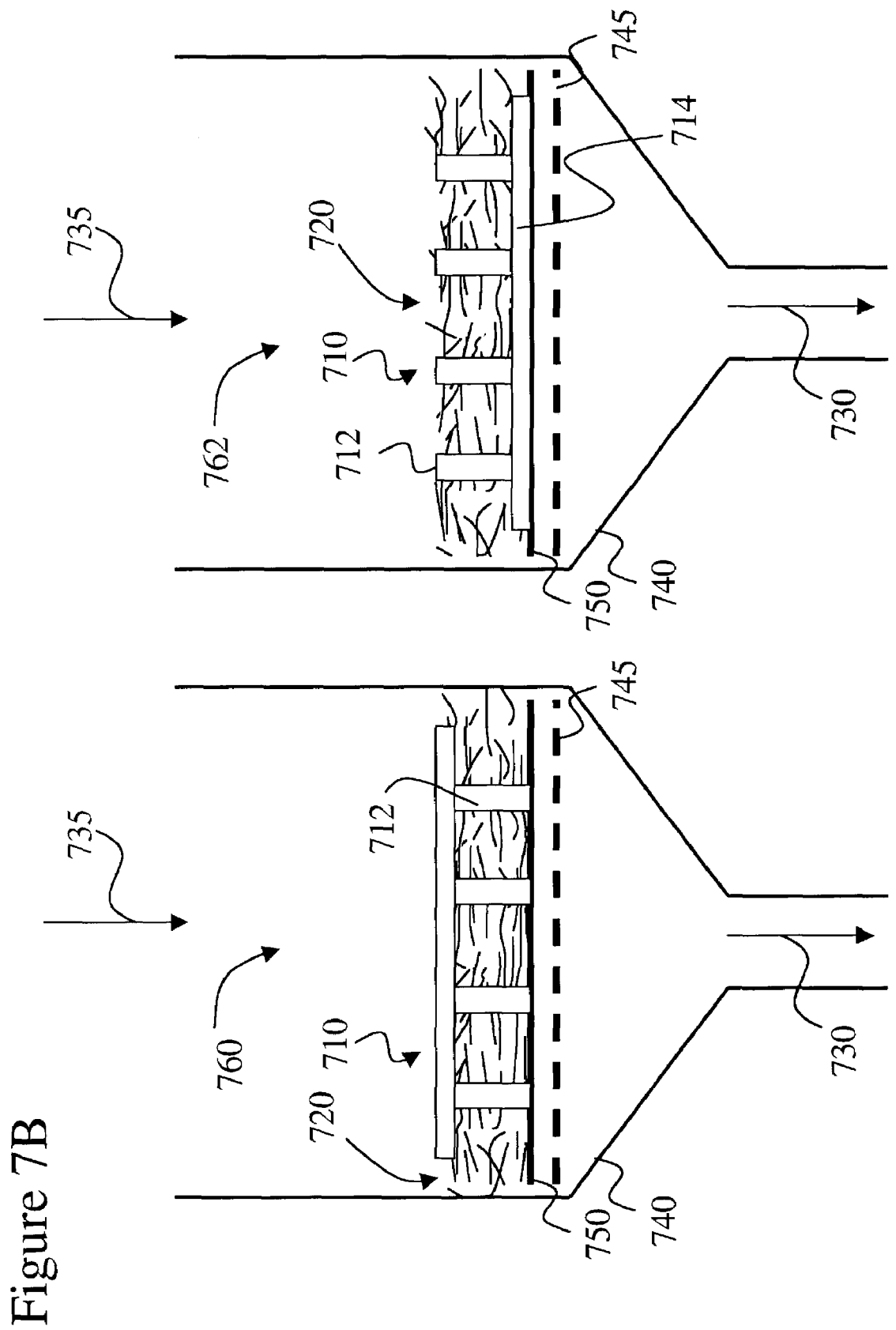

FIG. 7B shows an alternate exemplary method to make a nanotube mat with conduits that is described for illustration purposes only and should not be regarded as limiting to the scope of the present invention. This method combines the creation of the nanotube mat as described in FIG. 7A, while at the same time creating the conduits. Mold 710 could be positioned over filter 750. However a mold or the structures of a mold could also be sprayed on a filter or substrate, glued on a filter or substrate, or even be printed or stamped onto a filter or substrate or made using photolithography techniques. The present invention is not limited to any of these methods. The idea of mold 710 is to provide the structures 712 that will form the conduits once the slurry of carbon nanotubes is pulled down onto mold 710.

In one aspect mold 710 is placed in funnel 740 in such a manner that structures 712 of mold 710 that create the conduits are faced down toward and against filter 750. If one would like to create a nanotube mat with cups (i.e. partially through the nanotube mat), then structures 712 of mold 710 should be kept at a certain distance so that they are not placed directly against filter 750 (this could be accomplished by a support element or structure to allow enough space so that a mechanically stable cup can be created, this is not shown). In another aspect, mold 710 is placed in funnel 740 in such a manner that the base 714 of mold 710 is placed against filter 750. However, in this case it would be preferred that base 714 has filter-like properties to filter the liquid from the slurry while disallowing passage of the carbon nanotubes. The slurry of carbon nanotubes 720 is either placed in between mold 710 and filter 750 or over mold 710 and in between structures 712 as shown by 760, 762 respectively. After pulling or pushing down the slurry of carbon nanotubes 720, the nanotube mat needs to be removed from the mold and/or filter. This removal could be assisted by peeling or cutting the nanotube mat from the mold (and/or filter), or by any other method known in the art that would assist in this removal process if needed.

Figure 9:
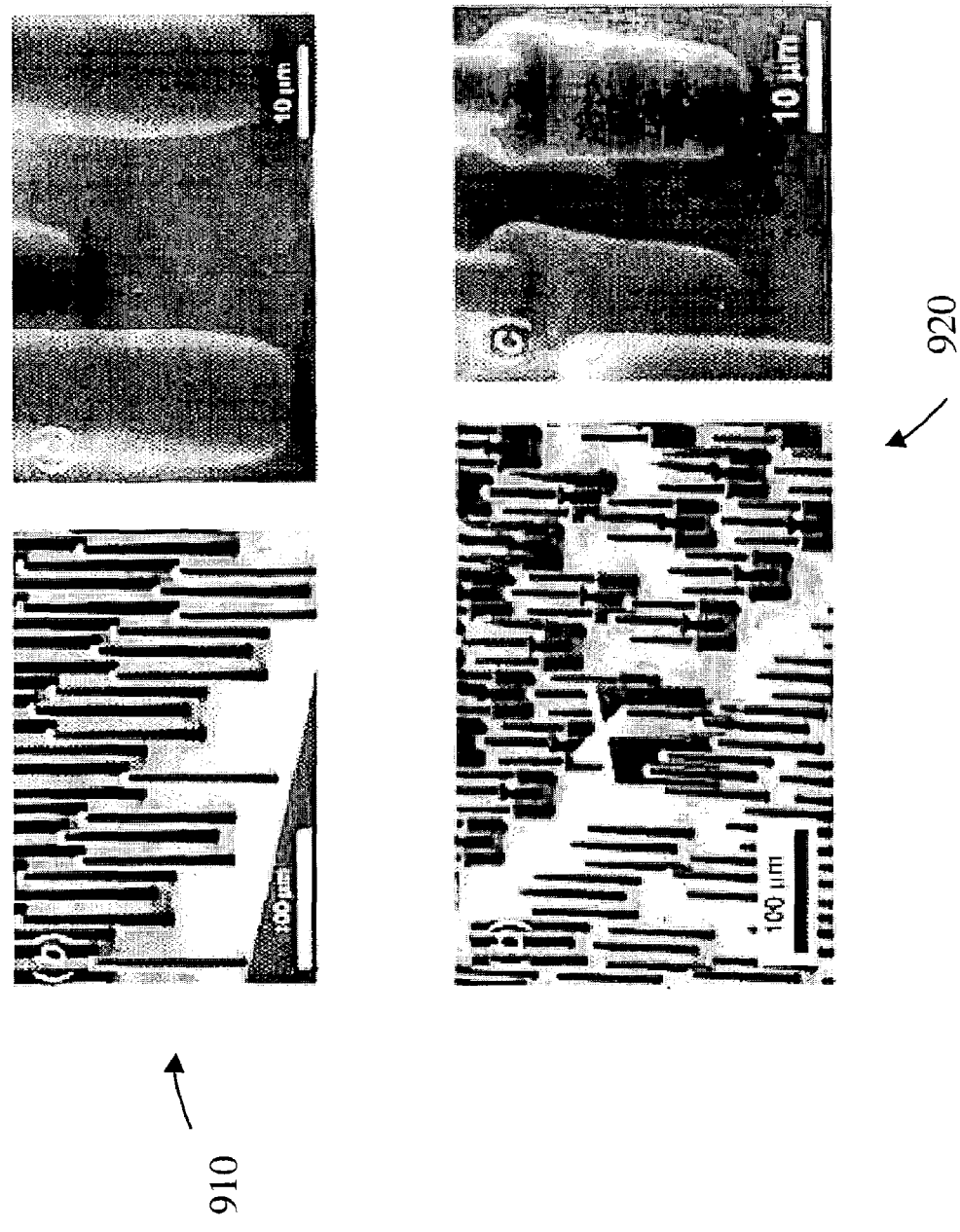
FIG. 9 shows scanning electron micrographs of molds based on an exemplary photolithography method of making a mold.
Figure 10:
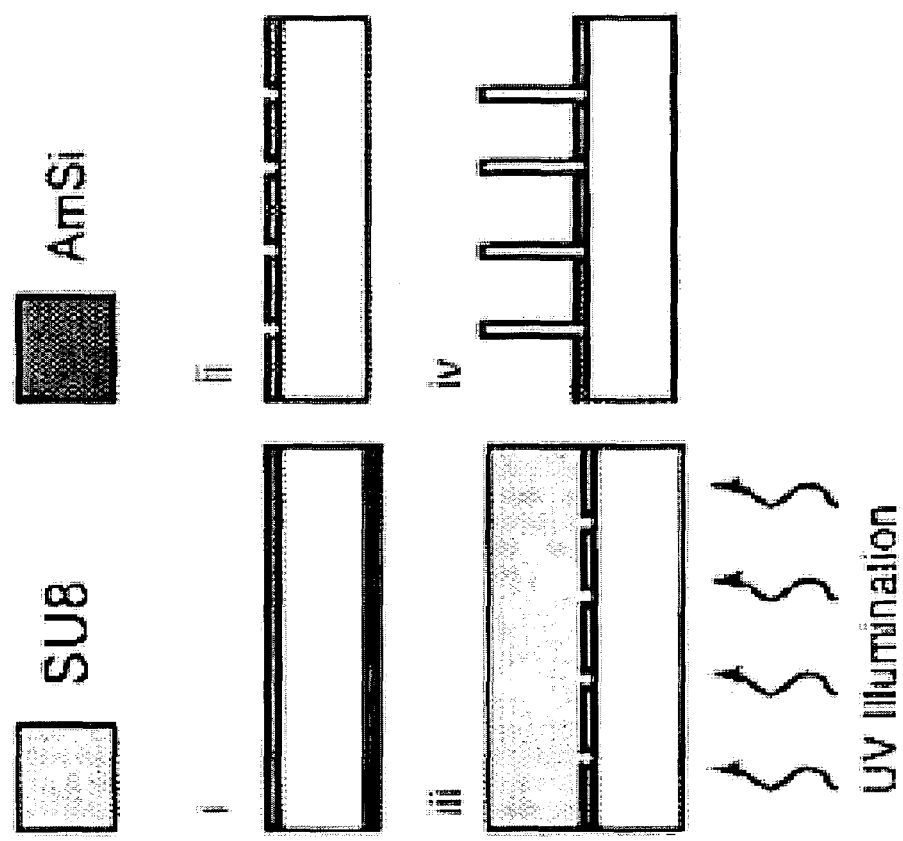
FIGS. 10-11 show exemplary photolithography methods of making a mold.

FIG. 9 shows a scanning electron micrograph of exemplary molds based on photolithography to produce pillars 910 and pillars 920 with two different diameters (For details see a paper by *Peterman et al.* (2003) entitled "*Building thick photoresist structures from the bottom up*" and published in *J. Micromech. Microeng.* 13:380-382, which is hereby incorporated by reference). The latter structure 920 could be considered as a multi-layered structure having a pillar on top of a cup. The method of making a mold with cups, pillars or walls using photolithographic techniques could include the following steps as shown in FIG. 10, which is described for illustrative purposes only and should not be regarded as limiting to the present invention. For instance, a four-inch Schott Borofloat R wafers, e.g. 700 microns thick, could be obtained with e.g. 1500 Angstrom of amorphous silicon already in place. The amorphous silicon could be patterned lithographically using 1 µm AZ3612 photoresist. Reactive ion etching (SF6/F-115) will transfer the pattern to the amorphous silicon, after which the AZ3612 was stripped in acetone. SU-8 2100 (MicroChem Corp.) could be spun on the wafer (e.g. 100-300 µm) and baked according to the manufacturer's specifications. The wafer could be inserted into an aligner upside down, with the SU-8 toward a vacuum chuck. The exposure time could be chosen to yield a dosage 150% higher than the recommended dosage, to develop tall as possible structures. The exposures could be pulsed, typically 10 seconds on followed by 5 seconds off, to allow the resist to relax between doses. Development could be performed in either PGMEA (SU-8 developer) or in ethyl lactate (SU-8 thinner) as supplied by MicroChem Corporation.

Figure 11:
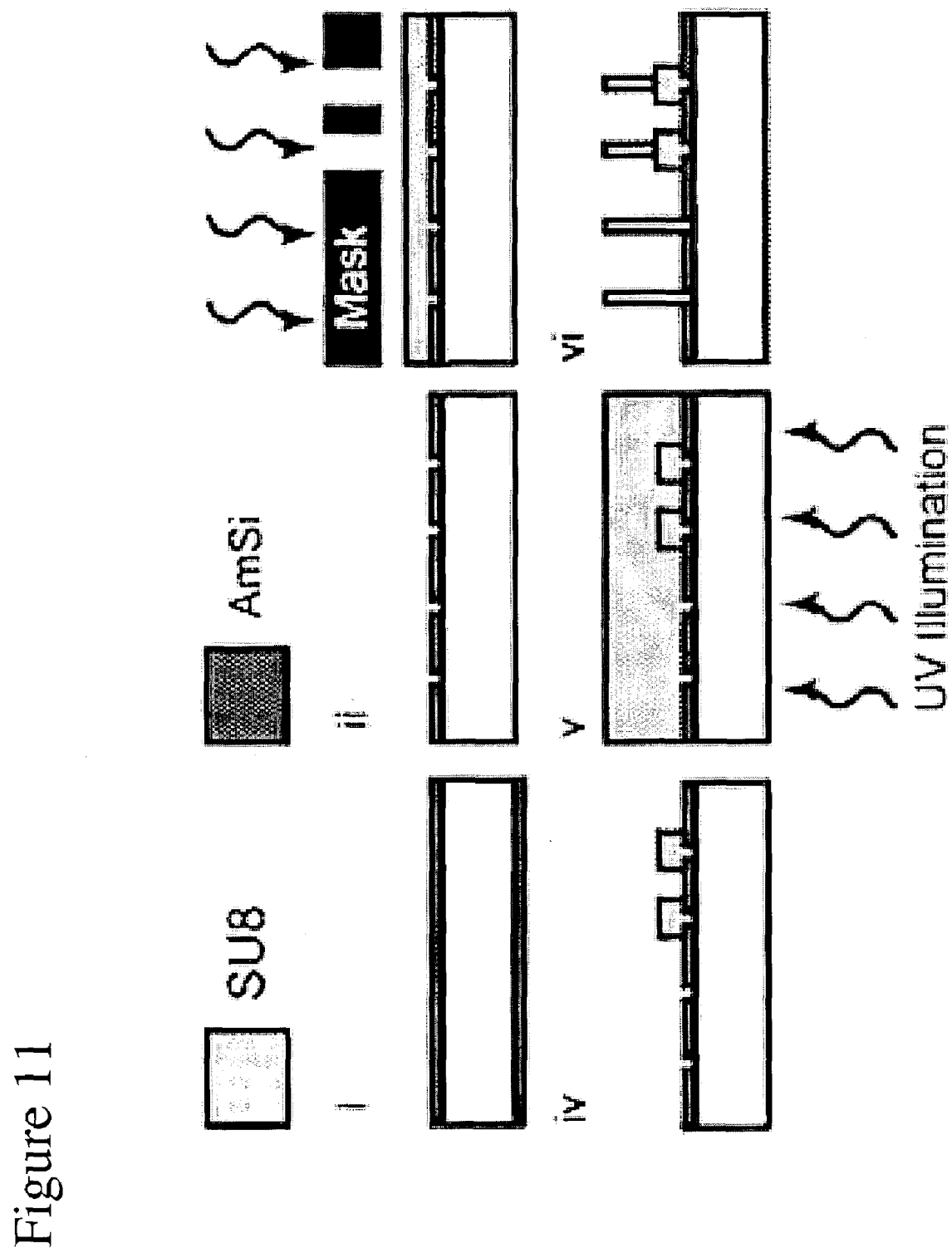

Following the photolithographic method steps as described with respect to FIG. 10, the methods steps could progress similarly as shown in FIG. 11 to develop multi-layered molds such as shown by 920. After the mask was defined in the amorphous silicon and the photoresist stripped, a layer of SU-8 2050 (e.g. 25-50 µm) could be spun on the wafer. This layer could then be exposed from the top, just as in standard topside lithography, with alignment to the features etched in the silicon. After development, a second layer of thick photoresist (e.g. 100-300 µm) could be spun onto the wafer, and exposed from the backside of the wafer.

Figure 12:
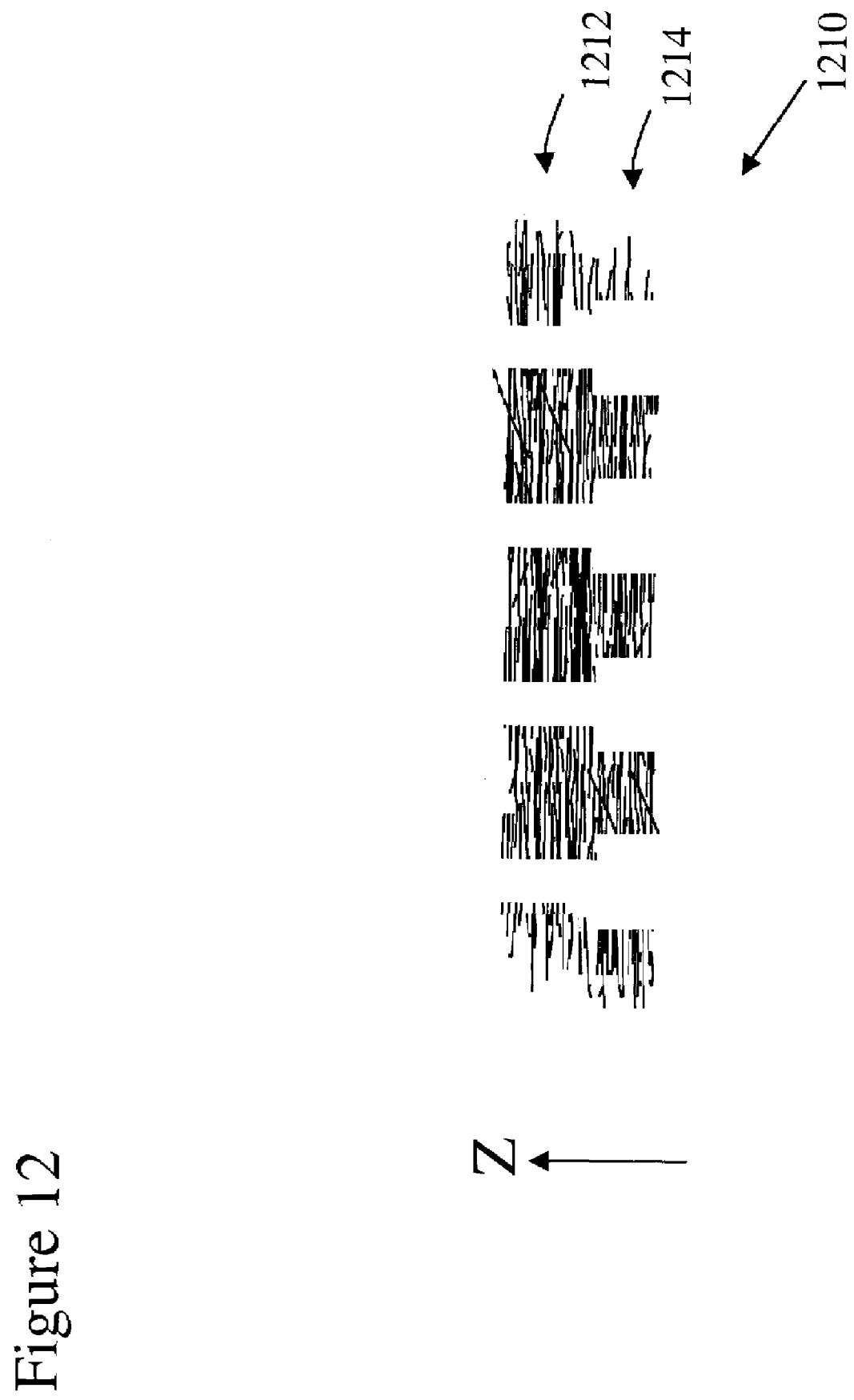
FIG. 12 shows a multi-layered structure of conduits based on multi-layered nanotube mats according to the present invention.

FIG. 12 shows an another method of developing multi-layered structures that is based on a multi-layered nanotube mat 1200, whereby each individual nanotube mat 1212, 1214 could provide a different size and/or different shape of conduit. The example of FIG. 12 shows a two-layered device, however, the present invention is not limited to two layers and could in general include two or more individual nanotube mats. The individual nanotube mats could be glued together, sutured together or held together by a mechanical means.

Figure 13:
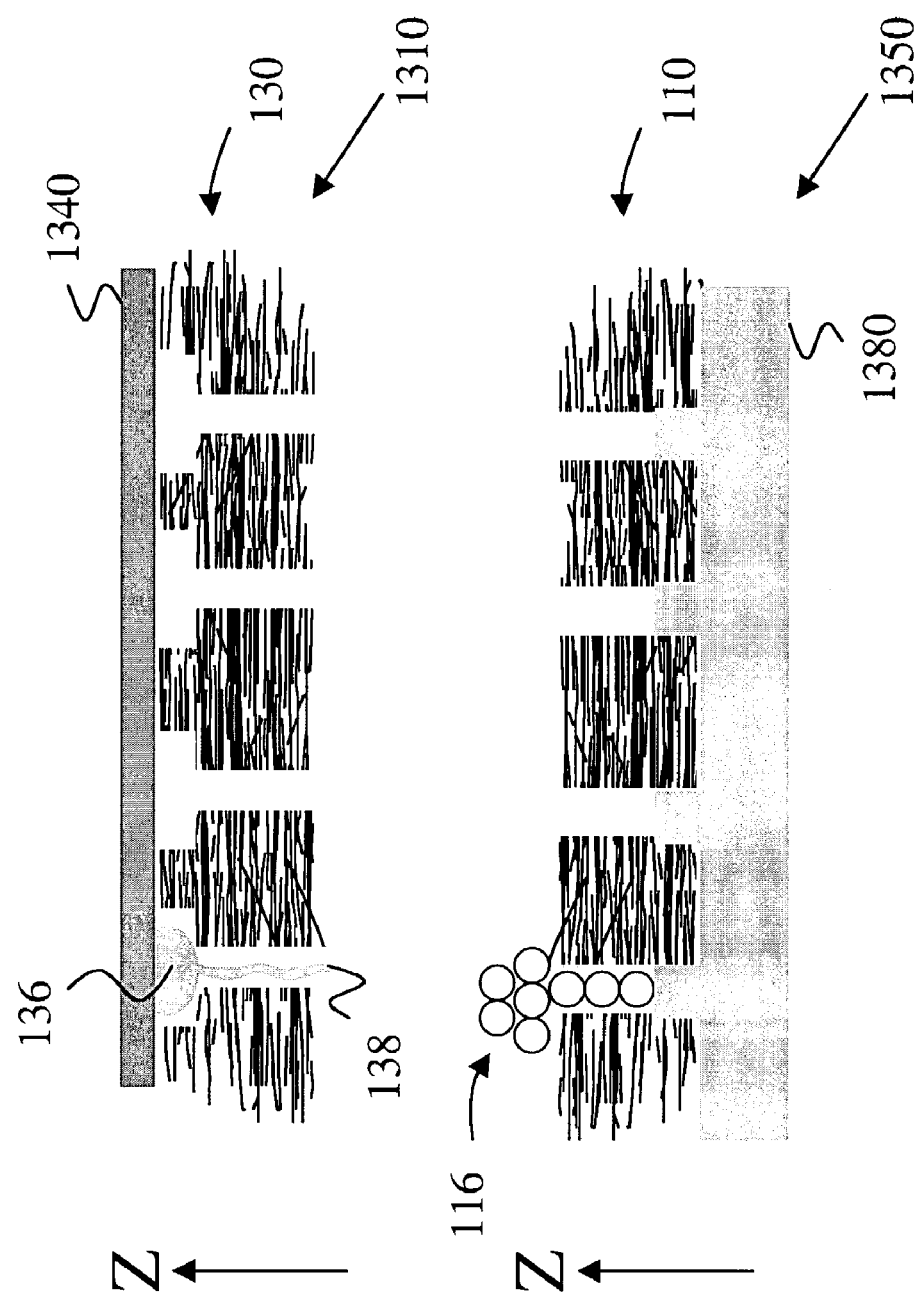
FIG. 13 shows examples of a nanotube mat interfaced with a device or structure according to the present invention.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. For instance, FIG. 13 shows two examples 1310, 1350 of using a nanotube mat 110, 130 (shown in FIG. 1) as an interface for a structure or device 1340, 1380, respectively. Structure 1380 could e.g. protrude into the conduit(s) and therewith interface with a cell or cell process. Furthermore a ligand could be placed inside a conduit and used to bind cells. Structure or device 1340, 1380 could have a monitoring means, controlling means, stimulating means and/or an additional interfacing means which could either include an electrical, a chemical, a mechanical, an optical or a magnetic means. Interfacing or integrating the nanotube mat(s) with different cells, tissue or devices allows one to develop various kinds of prosthetic interfaces and systems leading to several types of applications, which are described infra for exemplary purposes only and the present invention should not be regarded as limited to these examples.

In one aspect, different types of animal or human cells could be arrayed. For instance, neurons could be arrayed that would allow a complementary array of cell stimulators (e.g. chemical, electrical, optical, magnetic, or the like) to address arrayed neurons singly or in patterns. Cells could also be sorted whereby a mixture of cells is allowed to self assemble into a defined pattern of the nanotube mat. Cells could be arranged into their natural pattern or the nanotube mat could play an active role in creating a pattern of cells. Furthermore, for instance ligands, inhibitory factor, growth factors or the like could play a role in such cell patterning. In one application, a cell phenotype could be observed. In another application one could co-culture cells that have specific cell-cell (close proximity) interactions for (i) the development of specific cell types where co-culturing is important, for instance in a controlled incubator, (ii) as a scientific platform to study cell-cell interactions, (iii) develop neuronal circuits or logic circuits to, for instance, use on/off cell types found in the retina, (iv) for drug evaluation, for instance, for cell-cell interaction on an easily accessible nanotube mat or (v) for drug toxicity evaluation whereby populations of arrayed cells can be evaluated easily on an accessible nanotube mat.

In another aspect, single cells could be arrayed. For instance, in applications related to evaluating drug metabolism, such a single cell analysis would be useful because the cells are easily accessible on a defined array. One could monitor (i) gene activation, (ii) biochemical and enzyme activation, (iii) cell products, or (iv) phenotypic changes. In another application related to drug toxicity populations of cells could be arranged and evaluated in an array.

In yet another aspect, whole cells could be arrayed whereby the diameter of the conduits (channels) through the nanotube mat may be made to accommodate whole cells and align the main axis of the cells in a predetermined direction or perpendicular to the plane of the membrane. An example of such a cell is a cylindrical photoreceptor cell.

In still another aspect, the nanotube mats could be used for diagnostic purposes. For example, sentinel cells that have different sensitivities to metabolites, xenobiotics, and analytes could be arranged in a defined pattern and could be monitored for changes in phenotype or viability. These sentinel cells may have genes that turn on a visible green fluorescent protein or luciferin/luciferase or heat shock protein when activated or stressed.

In still another aspect, the nanotube mats could be used to monitor immune responses. For example, this could be accomplished in vivo since a nanotube mat is minimally immunogenic and can be engineered to different densities. An array of different test cells could be implanted into a host and monitored for rejection or inflammation. This could also be accomplished in vitro by, for example, a prospective host macrophage or host immune cells that may be used to challenge different cell types from prospective donors. In still another aspect, the nanotube mats could be used to pick out and isolate virally transfected cells from cells that have not been transfected.

In still another aspect, the nanotube mats could be used as a semiconductor-cell interface or sensor. For example, a light pipe pushed up against a cell that produces a metabolic product when light is 'on' or a cell that doesn't produce a metabolic product when light is 'on' could be interfaced with the nanotube mat. Another example relate to a cell that glows when stressed or detects an analyte. The light pipe/light sensor detects this change in illumination or the cell stops glowing when dead or stressed and light pipe no longer sees a glow.

In still another aspect, one could develop applications related to neural circuits or neural computing networks, for instance, when two or more nanotube mats are sandwiched together. Cell types can be defined and arranged in a defined array. Because of the plasticity of synaptic connections, a multilaminate array of neurons could be taught to react in predictable ways. The multilaminate array could learn in an un-supervised manner and could synthesize novel solutions. Another example of using multi-layered nanotube mats relates to building an artificial retina. The retina is made up of discrete layers of cells that interact with one another. By seeding each layer of nanotube mats with the appropriate population of cells, one could build a device that resembles a retina. Furthermore, in another application related to brain functions as well as the layered and discrete structure of the brain, one could seed different layers of nanotube mats with defined populations of cells to mimic or repair this type of tissue or any other type of tissue that form different layers. In still another aspect, the nanotube mat(s) could be used as layer(s) for tissue repair or as a prosthetic device.

The present invention is not limited to biological cells since the conduits could hold living, chemicals, analytes, drugs, lipids, carbohydrates, secretory products or the like. The density and biochemical properties of the nanotubes/nanotube mat may be varied to mimic the physiological properties of native basement membranes. The nanotube mat could also be derivatized with growth factors, molecules, nutrients, ligands, transduction molecules, inhibitory factors or morphogenic factors before it is used for the support, organization, growth or interfacing of biological cells, which could be placed inside a conduit. The electrical properties of the nanotubes/nanotubes mat may be used to enhance the biological properties of the nanotubes mat, for example, self-cleaning by altering the electrical charge of the mat. All such variations are considered to be within the scope and spirit of the present invention as defined by the following claims and their legal equivalents.

What is claimed is:

1. A device to direct growth of biological cells, comprising a nanotube mat wherein said nanotube mat comprises an array of conduits through the thickness of said nanotube mat, wherein said conduits are sized to accommodate said growth of at least one of said biological cells.

2. The device as set forth in claim 1, wherein said conduits are channels, discontinuous channels, tapered channels or channels with two different diameters.

3. The device as set forth in claim 1, wherein the surface of said nanotube mat is derivatized with growth factors, nutrients, inhibitory factors, ligands or morphogenic factors.

4. The device as set forth in claim 1, wherein said biological cells comprise different types of biological cells and said conduits are sized to accommodate said different types of biological cells.

5. A device to host biological cells, comprising a nanotube mat wherein said nanotube mat comprises an array of conduits partially through the thickness of said nanotube mat, wherein said conduits are sized to host at least one of said biological cells.

6. The device as set forth in claim 5, wherein said conduits are channels, discontinuous channels, tapered channels or channels with two different diameters.

7. The device as set forth in claim 5, wherein the surface of said nanotube mat is derivatized with growth factors, nutrients, inhibitory factors, ligands or morphogenic factors.

8. The device as set forth in claim 5, wherein said biological cells comprise different types of biological cells and said conduits are sized to accommodate said different types of biological cells.

9. The device as set forth in claim 6, wherein one of said two different diameters is sized to accommodate at least one of said biological cells, and wherein the other of said two different diameters is sized to accommodate at least one neurite.

10. The device as set forth in claim 1, wherein said biological cells are patterned on the surface of said nanotube mat.

11. A device to control delivery of an agent, comprising a nanotube mat wherein said nanotube mat comprises an array of conduits through the thickness of said nanotube mat, wherein said conduits are sized to accommodate the delivery of said agent.

12. The device as set forth in claim 11, wherein said agent is a chemical, a drug, a protein, a lipid or a carbohydrate.

13. The device as set forth in claim 11, wherein said conduits are channels, discontinuous channels, tapered channels or channels with two different diameters.

14. The device as set forth in claim 11, wherein biological cells are patterned on the surface of said nanotube mat.

15. A prosthetic device, comprising a nanotube mat wherein said nanotube mat comprises an array of conduits through the thickness of said nanotube mat, wherein said conduits are sized to support or grow biological cells.

16. The prosthetic device as set forth in claim 15, wherein said biological cells are neural cells.

17. The prosthetic device as set forth in claim 15, wherein said conduits are channels, discontinuous channels, tapered channels or channels with two different diameters.

18. The prosthetic device as set forth in claim 15, wherein the surface of said nanotube mat is derivatized with growth factors, nutrients, inhibitory factors, ligands or morphogenic factors.

19. The prosthetic device as set forth in claim 15, wherein said biological cells comprise different types of biological cells and said conduits are sized to accommodate said different types of biological cells.

20. The prosthetic device as set forth in claim 17, wherein one of said two different diameters is sized to host at least one of said biological cells, and wherein the other of said two different diameters is sized to accommodate at least one neurite.

21. The device as set forth in claim 15, wherein said biological cells are patterned on the surface of said nanotube mat.

22. A device to direct growth of neurites, comprising a nanotube mat wherein said nanotube mat comprises an array of conduits through the thickness of said nanotube mat, wherein said conduits are sized to accommodate said growth of at least one of said neurites.

23. The device as set forth in claim 22, wherein said conduits are channels, discontinuous channels, tapered channels or channels with two different diameters.

24. The device as set forth in claim 22, wherein the surface of said nanotube mat is derivatized with growth factors, nutrients, inhibitory factors, ligands or morphogenic factors.

25. The device as set forth in claim 22, wherein said neurites are patterned on the surface of said nanotube mat.

26. A device to host neurites, comprising a nanotube mat wherein said nanotube mat comprises an array of conduits partially through the thickness of said nanotube mat, wherein said conduits are sized to host of at least one of said neurites.

27. The device as set forth in claim 26, wherein said conduits are channels, discontinuous channels, tapered channels or channels with two different diameters.

28. The device as set forth in claim 26, wherein the surface of said nanotube mat is derivatized with growth factors, nutrients, inhibitory factors, ligands or morphogenic factors.

29. The device as set forth in claim 26, wherein said neurites are patterned on the surface of said nanotube mat.

30. A prosthetic device to host growth of neurites cell, comprising a nanotube mat wherein said nanotube mat comprises an array of conduits partially through the thickness of said nanotube mat, wherein said conduits are sized to accommodate said growth of at least one of said neurites cell.

31. The prosthetic device as set forth in claim 30, wherein said conduits are channels, discontinuous channels, tapered channels or channels with two different diameters.

32. The prosthetic device as set forth in claim 30, wherein the surface of said nanotube mat is derivatized with growth factors, nutrients, inhibitory factors, ligands or morphogenic factors.

33. The prosthetic device as set forth in claim 30, wherein said neurites are patterned on the surface of said nanotube mat.

* * * * *